United States Patent
Paton et al.

[11] Patent Number: 6,072,568
[45] Date of Patent: *Jun. 6, 2000

[54] THERMAL BARRIER COATING STRESS MEASUREMENT

[75] Inventors: Neil E. Paton, N. Muskegon; Kenneth S. Murphy, Muskegon, both of Mich.; David R. Clarke, Santa Barbara, Calif.

[73] Assignee: Howmet Research Corporation, White Hall, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/810,001

[22] Filed: Mar. 3, 1997

[51] Int. Cl.$^7$ .................................................. G01N 21/64

[52] U.S. Cl. ................................ 356/32; 73/800

[58] Field of Search .................. 356/32, 327; 73/800

[56] References Cited

U.S. PATENT DOCUMENTS

| | | | |
|---|---|---|---|
| 4,405,659 | 9/1983 | Strangman | 427/248 |
| 4,460,274 | 7/1984 | Schumann et al. | 356/318 |
| 4,492,121 | 1/1985 | Lehto | 73/705 |
| 4,676,994 | 6/1987 | Demaray | 427/42 |
| 4,774,150 | 9/1988 | Amano et al. | 428/690 |
| 4,805,461 | 2/1989 | Gupta et al. | 73/800 |
| 5,015,502 | 5/1991 | Strangman et al. | 427/248 |
| 5,238,752 | 8/1993 | Duderstadt et al. | 428/623 |
| 5,438,402 | 8/1995 | Gupta | 356/35.5 |
| 5,490,426 | 2/1996 | Shiga et al. | 73/762 |
| 5,514,482 | 5/1996 | Strangman | 428/623 |
| 5,606,171 | 2/1997 | Neckers et al. | 250/459.1 |

OTHER PUBLICATIONS

"Residual Stress Measurement in Sapphire Fiber Composites: Through-Focus and Transmission Fluorescence Spectroscopy" Fracture Mechanics, 25th vol., ASTM, pp. 241–254, 1995, Lipkin and Clarke.

"Stress Development in Alumina Scales Formed Upon Oxidation of (III) NiAl Single Crystals", Corrosion Science, vol. 39, pp. 231–242, Feb. 1997 Lipkin et al.

"Nondestructive Evaluation of the Oxidation Stresses Through Thermal Barrier Coatings Using $Cr^{3+}$ Piezospectroscopy" Appl. Phys. Lett. vol. 69, No. 24, Dec. 9, 1996, Christensen et al.

"Stress Measurement Using Optical Fluorescence" Qing Ma et al., AMD–vol. 181, Experiments in Smart Materials and Structures, pp. 27–37, 1993.

Primary Examiner—Richard A. Rosenberger
Attorney, Agent, or Firm—Edward J. Timmer

[57] ABSTRACT

A non-destructive measurement method for determining residual stress proximate an intermediate layer in a multi-layer thermal barrier coating system by directing a laser beam through an outer ceramic thermal insulating layer with the laser beam illuminating a ceramic-bearing intermediate layer in a manner to cause species present in the intermediate layer to fluoresce, measuring the frequency of the light or photons emitted by the fluroescing species, and comparing the measured frequency shift of the intermediate ceramic layer to the frequency shift determined on like ceramic material under controlled stress states to determine a representation of relative residual stress in the measured coating. The invention can be used to assess integrity or quality control of as-manufactured TBC coatings or to assess remaining coating service life of engine-run TBC coated components during an inspection or repair procedure.

10 Claims, 2 Drawing Sheets

THERMAL BARRIER COATING STRESS MEASUREMENT

FIELD OF THE INVENTION

The present invention relates to non-destructive measurement of residual stress of a layer of a multilayer thermal barrier coating system.

BACKGROUND OF THE INVENTION

Thermal barrier coating systems for components, such as blades and vanes, used in gas turbine engines are the subject of numerous patents including, but not limited to, U.S. Pat. Nos. 4,405,659; 4,676,994; 5,015,502; and 5,514,482. Thermal barrier coating systems typically are applied on a superalloy substrate and involve an inner bondcoat on the substrate, an outer thermal insulating layer which typically comprises one or more ceramic materials, and a thin intermediate ceramic layer located between the bondcoat and the thermally insulating layer to promote adherence of the thermally insulating layer. A typical TBC coating system uses an alumina (aluminum oxide) intermediate layer between a ceramic (e.g. zirconia stablized with yttria) thermal insulating layer and a metallic and/or diffusion aluminide bondcoat.

In such TBC coating systems, spallation of the outer thermal insulating layer can occur at the intermediate layer as a result of residual compressive stresses in the TBC system, especially between the bond coat and intermediate layer. This is especially true of TBC systems where the thermal insulating layer is electron beam evaporated and physical vapor deposited (EB-PVD) on an intermediate ceramic layer, such as alumina. The influence of residual compressive stresses in thermal barrier coating (TBC) systems is closely linked to TBC adherence properties observed in testing and service.

Residual stress measurement techniques such as X-ray diffraction have been of limited use in determining residual compressive stress of TBC systems due in large part to the difficulty in penetrating through the thermal insulating layer to the intermediate layer. The intermediate layer also is very thin (e.g. 1 micron thickness) and is therefore very difficult to characterize by X-ray diffraction and other conventional techniques such as neutron diffraction.

An object of the present invention is to provide a non-destructive measurement method for determining residual stress proximate an intermediate layer in a multilayer a TBC coating system.

Another object is to provide a a quality control procedure or repair that uses such residual stress measurement as a means for determining acceptability of a manufactured TBC coating system for service or of an engine-run TBC coating for return to service during inspection or repair procedures.

SUMMARY OF THE INVENTION

The present invention involves a non-destructive measurement method for determining residual stress proximate an intermediate layer, which for example only typically is a ceramic material, in a multilayer TBC coating system by directing a laser beam through the outer thermal insulating layer with the laser beam illuminating the intermediate layer in a manner to cause species present in the intermediate layer to fluoresce, measuring the frequency of the light (photons) emitted by the fluroescing species, and comparing the measured frequency shift of the intermediate layer to the frequency shift determined on a reference material comprising, for example only, ceramic material when the intermediate layer is ceramic material, under controlled stress states to assess or determine a relative residual stress in the measured coating.

In an embodiment of the invention applicable to TBC coating systems having an alumina intermediate layer formed on a bondcoat layer, the laser beam is directed through an outer ceramic layer and focused on the intermediate alumina layer in a manner to cause Cr ion impurities (species) present in the alumina layer to fluoresce. The frequency shift of light (photons) emitted by the fluorescing Cr ion impurities is measured by, for example, a spectrometer, and the frequency shift of the measured TBC coating is compared to a predetermined relationship between frequency shift and compressive stress determined from bulk alumina specimens to assess residual compressive stress in the measured coating. The alumina specimens used to determine the aforementioned relationship contain similar fluorescing impurities and are subjected to controlled amounts of compressive stress to determine the aforementioned relationship between frequency shift and compressive stress in the alumina specimens.

Another method embodiment of the invention involves assessing integrity or quality control of as-manufactured TBC coatings by measuring residual stress in the manner described. Still another method embodiment of the invention involves assessing the remaining coating service life of engine-run TBC coated components during an inspection or repair procedure by measuring residual stress in the manner described. Advantageously, the assessments can be made in a non-destructive manner pursuant to the invention.

The above objects and advantages of the present invention will become more fully apparent from the following detailed description taken with following drawings.

DESCRIPTION OF THE INVENTION

Figure 1:
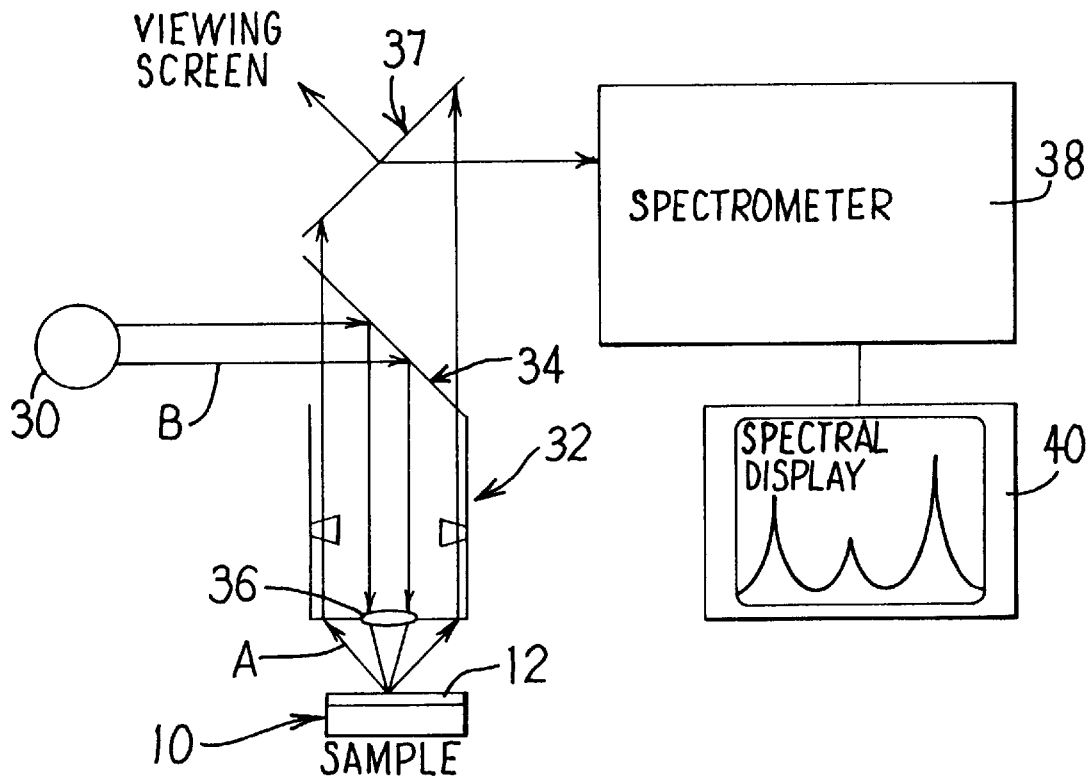
FIG. 1 is a schematic diagram of a measurement apparatus useful for practicing the invention to assess residual stress in a TBC coating system on a substrate.
Figure 2:
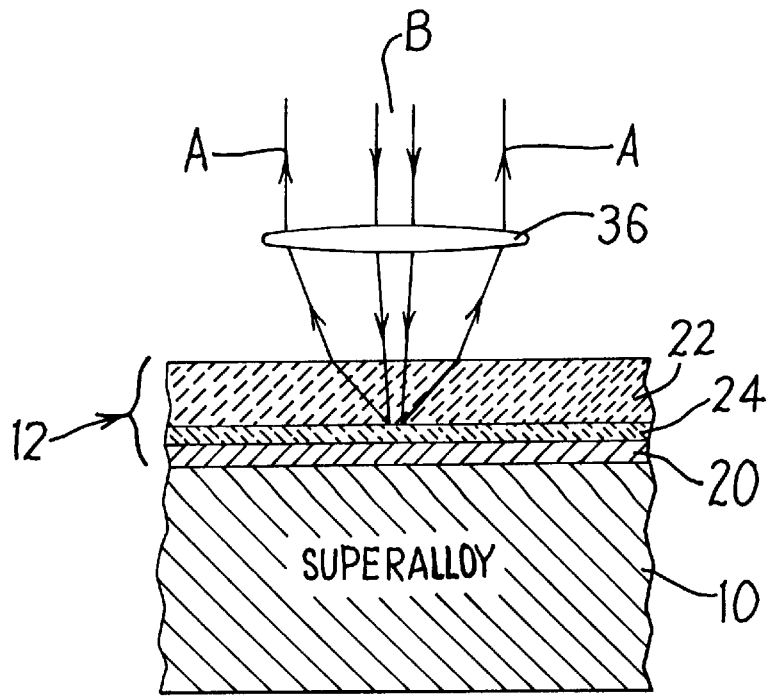
FIG. 2 is an enlarged view of the apparatus and TBC coated substrate.

Referring to FIGS. 1 and 2, measurement apparatus useful for practicing the invention to measure or assess residual stress in a TBC coating system 12 on a superalloy substrate 10 is schematically illustrated. The TBC coating 12 typically comprises an inner bondcoat 20, outer thermal insulating layer 22, and intermediate layer 24. The inner bondcoat 20 may comprise a metallic layer, such as an MCrAlY alloy layer, a diffusion nickel aluminide layer which may be modified by inclusion of Pt or other precious metals, Cr, and other additions and formed by chemical vapor deposition, pack cementation, and other well known techniques, and above-the-pack, slurry, sputtering, carhodic arc, electron beam evaporation, and the like. The bondcoat layer typically ranges in thickness from about 1 mil to about 5.0 mils for purposes of illustration. Additionally, if the superalloy is an alumina former, the bondcoat may be omitted with the superalloy forming an in-situ alumina layer. Or, alumina may be applied to the superalloy as a layer.

The outer thermal insulating layer 22 typically comprises a ceramic material such as zirconia and other known ceramic materials which may be modified by inclusion of other ceramic materials such as yttria, ceria, scandia, magnesia, and similar materials. The outer thermal insulating layer may be a graded layer that changes composition from proximate the intermediate layer 24 to the outer surface of the thermal insulating layer as is well known. The thermal insulating layer typically is applied to the intermediate layer 24 by electron beam PVD (physical vapor deposition) where ceramic material is evaporated by electron beam heating and vapor deposited on the substrate at elevated coating temperature. When applied by electron beam PVD, the thermal insulating layer 22 exhibits a microstructure of columnar grains extending generally perpendicular to the substrate surface. The thermal insulating layer typically ranges in thickness from about 2 mils to about 20 mils for purposes of illustration only.

The intermediate layer 24 can be formed by oxidation of the bondcoat by heating in an oxidizing atmosphere to thermally grow the layer thereon as a thin oxide layer. Alternately, the intermediate layer can be deposited by chemical vapor deposition on the bondcoat as a thin layer of ceramic material. The intermediate layer typically comprises predominantly ceramic material such as alumina. The intermediate layer 24 typically includes metallic impurity species, e.g. Cr ion impurities, from the underlying substrate/bondcoat when the intermediate layer is thermally grown on the bondcoat. If the intermediate layer is chemical vapor deposited at elevated temperature, Cr from the substrate/bondcoat can be present as an impurity as the intermediate layer is deposited. The intermediate layer typically ranges in thickness from about 0.1 to about 10 microns for purposes of illustration only.

TBC coatings of the type described are well known and described in such patents as U.S. Pat. Nos. 4,405,659; 4,676,994; 5,015,502; and 5,514,482 as well as others.

The invention involves a non-destructive measurement method for determining relative residual stress proximate the intermediate layer 24 of a multilayer TBC coating by directing a laser beam through the outer thermal insulating layer 22 with the laser beam focused on the intermediate layer 24 in a manner to cause species present in the intermediate layer to fluoresce. The frequency of the light or photons emitted by the fluroescing species is measured and compared to the frequency of light or photons determined from bulk alumina reference specimens subjected to known compressive stresses to assess frequency shift that is representative of residual stress in the measured coating. The reference specimens contain similar fluorescing impurities and are subjected to controlled amounts of compressive stress to determine the relationship between frequency shift and compressive stress in the alumina specimens.

An exemplary TBC coating system offered for purposes of illustration and not limitation typically is applied to a nickel base superalloy substrate which for purposes of illustration only comprises a nickel base superalloy having a nominal composition of 0.05% C-1.5% Mo-6.5% Ta-0.004% B-7% Cr-7.5% Co-6.2% Al-0.15% Hf-3% Re-balance Ni where %'s are weight percents. The TBC coating comprises a bondcoat 20 comprising Pt—Al intermediate phase bondcoat having a composition 22 weight % Al-16% weight Pt-balance Ni), an intermediate layer 24 comprising alumina thermally grown on the bondcoat, and outer thermal insulating layer comprising yttria stablized zirconia (7 weight % yttria-balance zirconia) ceramic electron beam-PVD deposited on the alumina layer 24. The laser beam is directed through the outer layer 22 and focused on the intermediate alumina layer 24 to cause Cr ion impurities (species) in the alumina layer 24 to fluoresce. The Cr ion impurity species are incorporated in the alumina intermediate layer 24 from the substrate superalloy by virtue of thermal growth of the layer 24 on the bondcoat in an oxidizing atmosphere pursuant to allowed copending patent application Ser. No. 08/407,224 now U.S. Pat. No. 5,716,720 the teachings of which are incorporated herein by reference.

Referring again to FIGS. 1 and 2, measurement apparatus useful for practicing the invention to measure or assess residual stress in a TBC coating system 12 on a superalloy substrate 10 is schematically illustrated. The apparatus comprises a laser beam source 30 for directing a low power continuous laser beam B (e.g. 0.05 watts for measurements) through a microscope objective 32 in the manner shown onto the TBC coating system 12 on the substrate 10. In particular, the laser beam B is directed from source 30 to a mirror 34 and then to a focusing lens 36 of the objective 32 that directs the beam through the outer thermal insulating layer 22 and focuses it on the intermediate layer 24 to illuminate the layer 24 at a small spot in one embodiment of the invention. The illuminated spot may be as small as 1 micron diameter at the outer thermal insulating layer 22 and will be enlarged at the intermediate layer 24 after passing through the outer thermal insulating layer 22. In an alternative embodiment of the invention, the outer thermal insulating layer 22 can be illuminated with a large area, unfocused laser beam to illuminate the intermediate layer 24 with the laser beam with collection lens and spectrometer used to collect the fluoresence from the intermediate layer 24 that is illuminated by the unfocused laser beam. In still another alternative embodiment of the invention, the laser beam can be directed at the TBC coating using a fiber optic (not shown) so as to illuminate the intermediate layer 24, and another fiber optic (not shown) with a lens on the front facing the layer 22 is used to collect the fluorescence from the intermediate layer 24 and transmit it to the spectrometer. The laser beam B passes through the outer thermal insulating layer 22 in these embodiments because the illumination laser and the excited fluoresence both have energies below the optical absorption edge of the zirconia thermal barrier coating.

The frequency of the laser beam is chosen to cause a species present in the intermediate layer 24 to fluoresce when the layer is excited by the laser beam. For example, when Cr ion impurity species are present in an alumina intermediate layer 24 as described above for the exemplary TBC coating system, the laser beam has a wavelength of 5143 angstroms available from an argon ion laser. The Cr ions present in the alumina intermediate layer are caused to fluorsece by impingement of such laser beam on the intermediate alumina layer 24 to excite the Cr ion species. Other laser beam frequencies would be chosen in the event a different species is present in the intermediate layer 24.

The light or photons emitted by the fluorescing species of the intermediate layer 24 (e.g. Cr ion impurity species in the exemplary embodiment) is directed as shown by the arrows A in FIG. 1 back through the objective 32 to a mirror 37 and then to a conventional wavelength dispersive spectrometer 38 where the frequency of the light or photons is determined by the spectrometer. Mirror 37 also may comprise a viewing screen for the operator of the apparatus to observe the area of the coating from which the measurement is to be obtained. The spectrometer 38 typically is connected to a suitable visual display device 40, such as a computer display device, that visually displays the spectral frequency of the light or photons from the fluorescing species in the intermediate layer 24. The measured spectral frequency is recorded on a computer disk for storage and subsequent data analysis as well as for record keeping purposes.

The apparatus of FIGS. 1 and 2 is described in more detail in the technical article by Qing Ma and David R. Clarke entitled "Stress Measurement Using Optical Fluoresence", AMD, Vol. 181, Experiments in Smart Materials and Structures, Editor: Kyung-Suk Kim, Book No. H00888, 1993 (The American Society of Mechanical Engineers), the teachings of which are incorporated herein by reference with respect to the apparatus involved.

In accordance with the invention, the frequency shift of the measured alumina layer of the TBC coating is compared to the frequency shift determined from reference specimens. The reference specimens can comprise free standing bulk alumina reference specimens (reference sample size of 2×4× 25 millimeters for example only) and also alumina reference single crystals (size of 140 microns in diameter and several milimeters in length). The reference specimens are subjected to known compressive stress states to determine frequency shift in response to the known stress states as a reference or standard. The reference specimens are subjected to the known compressive stresses in a manner described in the above technical article by Ma and Clarke.

Figure 3A:
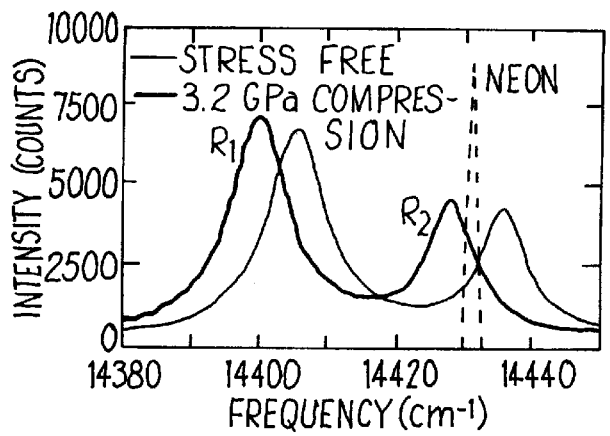
FIG. 3A is an illustrative depiction of frequency shift of light or photons from a reference bulk alumina sample with compressive stress and free of compressive stress.

For purposes of illustration, in FIG. 3A, the frequency shift of the free-standing alumina specimens in the unstressed state and the stressed state under 3.2 GPa compressive stress is illustrated. $R_1$ and $R_2$ are Cr fluorescing peaks. The lighter curve corresponds to the stress-free alumina bulk specimens while the darker curve corresponds to the stressed (3.2 GPa) alumina bulk specimens. In FIG. 3A, the frequency of a neon discharge line is shown as a calibration reference wavelength. FIG. 3A reveals a detectable frequency shift in light or photons emitted by the Cr ion impurity species present in the bulk alumina specimens from the application of compressive stress. The frequency shift results from residual compressive stress applied. This frequency shift allows assessment of the relative residual compressive stress present in an alumina layer of a TBC coating.

In particular, the relationship between the observed frequency shift and compressive stress in the bulk alumina specimens can be established pursuant to the present invention such that the relationship allows assessment of residual compressive stress present in a TBC coating simply by measuring the frequency shift as described above.

Figure 3B:
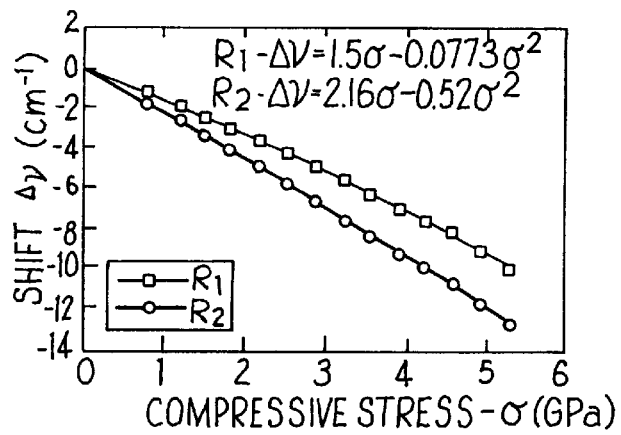
FIG. 3B is a graph of the frequency shift versus compressive stress for reference bulk alumina specimens.

For example, referring to FIG. 3B, the relationship between the observed frequency shift and compressive stress for the bulk alumina specimens described above at the different peaks $R_1$ and $R_2$ is shown over a range of compressive stresses of 0 to 6 GPa. Also shown are the mathematical relationships representing the curves shown where frequency shift, $\Delta v$, is related to compressive stress, sigma; i.e. for R1, $\Delta v = 1.50\sigma - 0.0773\sigma^2$ and for R2, $\Delta v = 2.16\sigma - 0.052\sigma^2$.

The established relationship between the observed frequency shift and compressive stress of the bulk alumina specimens allows assessment of residual compressive stress present in an alumina layer of a TBC coating having an unknown stress state or condition simply by measuring the frequency shift in the manner described above and determining the stress from the predetermined relationship such as shown in FIG. 3B.

In one embodiment of the invention, the integrity or quality control of as-manufactured (as-coated) TBC coatings of a particular type can be assessed by measuring residual stress in the manner described, determining the frequency shift, and then determining residual compressive stress in the coating in the manner described above using the relationship of compressive stress versus frequency shift. The measured residual stress in the TBC coating is compared to a specification range for residual stress to determine whether the coating is within or outside specification in this regard. Those TBC coated components falling outside the residual stress specification may be further treated by, for example, heat treatment, to produce residual stress within the specification range or not approved for actual service.

Figure 4:
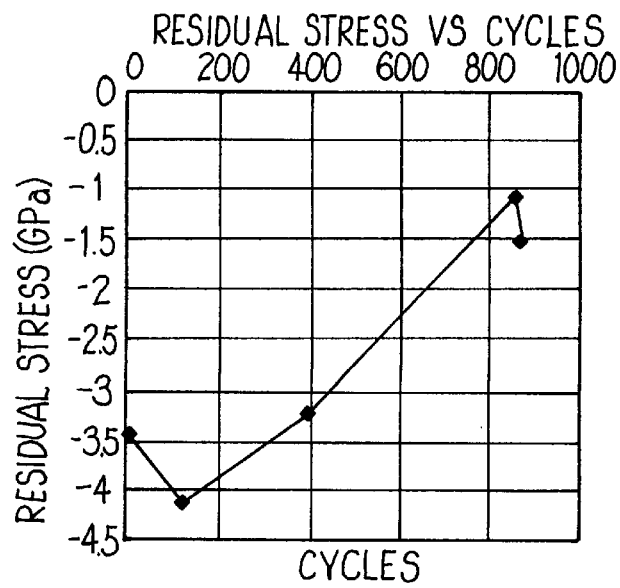
FIG. 4 is a graph of residual stress versus thermal cycles at 2075 degrees F.

In another embodiment of the invention, the remaining coating service life of engine-run TBC coated components that have been in service in, for example, a gas turbine engine can be assessed during an inspection or repair procedure by measuring residual stress in the manner described. The measured residual stress of the TBC coated engine-run components would determine a number of additional cycles of operation that the coating could withstand as shown in FIG. 4 to determine whether the coating is within or outside specification in this regard. In FIG. 4, cycles represents thermal cycle exposures to 2075 degrees F. Those TBC coated components exhibiting an additional number of cycles of service life (i.e falling within the residual stress specification for continued service) may be returned to further service in a gas turbine engine. Those TBC coated components falling outside the residual stress specification would not be returned to service and instead would be subjected to an overhaul procedure in which the components are refurbished including recoating with a new TBC coating.

Advantageously, in these embodiments of the invention, the assessments can be made in a non-destructive manner that does not damage or otherwise harm the TBC coating such that measured TBC coated components within the specification for residual stress can be approved for service or returned to service.

Although certain specific embodiments of the invention have been described hereabove, it is to be understood that modifications and changes may be made therein without departing from the spirit and scope of the invention as defined in the appended claims.

We claim:

1. A non-destructive measurement method for determining residual stress proximate a relatively thin intermediate ceramic layer in a multilayer thermal barrier coating having a relatively thick outer thermal insulating, different ceramic layer overlying said intermediate layer, and at least one of a bondcoat and superalloy substrate underlying said intermediate layer, comprising directing a laser beam to pass through said outer thermal insulating layer to illuminate said intermediate layer of said coating in a manner to cause species incorporated in said intermediate layer from at least one of said bondcoat and said superalloy substrate to fluoresce to emit light that passes back through said outer thermal insulating layer, measuring the frequency shift of the light emitted by the fluorescing species after it passes through said outer thermal insulating layer, comparing the measured frequency shift of said intermediate layer to the frequency shift determined on a reference material under controlled stress states to assess relative residual stress in the measured coating without need to remove said outer thermal insulating layer from said coating.

2. The method of claim 1 including comparing the measured frequency shift of an alumina intermediate layer of the coating to the frequency shift of an alumina reference sample determined under controlled stress states to determine relative residual stress in the measured alumina intermediate layer.

3. The method of claim 1 further including comparing said frequency shift of said intermediate layer to a predetermined relationship between frequency shift and stress of like bulk material to assess residual stress in said measured coating.

4. A non-destructive measurement method for determining residual stress proximate an intermediate ceramic layer comprising thermally grown alumina having a layer thickness of about 0.1 to about 10 microns in a multilayer thermal barrier coating having an outer thermal insulating layer comprising a different ceramic material overlying said intermediate layer, and at least one of a bondcoat and a superalloy substrate underling said intermediate layer, comprising directing a laser beam to pass through said outer thermal insulating layer with the laser beam illuminating said intermediate layer in a manner to cause chromium ion species incorporated in said intermediate layer from at least one of said bondcoat and said superalloy substrate to fluoresce to emit light that passes back through said outer thermal insulating layer, measuring the frequency shift of the light emitted by the fluorescing species after it passes through said outer thermal insulating layer, comparing the measured frequency shift of said intermediate alumina layer to the frequency shift of alumina reference material under controlled stress states to assess relative residual stress in the measured coating without need to remove said outer thermal insulating layer from said coating.

5. The method of claim 4 including comparing the measured frequency shift of the alumina intermediate layer of the coating to the frequency shift of bulk alumina determined under controlled stress states to determine a representative of residual stress in the measured alumina intermediate layer.

6. The method of claim 4 further including comparing said frequency shift of intermediate alumina layer to a predetermined relationship between frequency shift and stress of bulk alumina material to assess residual stress in said measured coating.

7. In the manufacture of multilayer thermal barrier coating, the steps of:

determining residual stress proximate a relatively thin intermediate ceramic layer in the manufactured multilayer thermal barrier coating which includes a relatively thick, outer thermal insulating, different ceramic layer overlying said intermediate layer and at least one of a bondcoat and superalloy substrate underlying the intermediate layer, by directing a laser beam to pass through said outer thermal insulating layer to illuminate said intermediate layer of said coating in a manner to cause species incorporated in said intermediate layer from at least one of said bondcoat and said superalloy substrate to fluoresce to emit light that passes back through said outer thermal insulating layer, measuring the frequency shift of the light emitted by the fluorescing species after it passes through said outer thermal insulating layer, comparing the measured frequency shift of said intermediate layer to the frequency shift determined on a reference material under controlled stress states to assess relative residual stress in the measured coating without need to remove said thermal insulating layer from said coating, comparing the assessed residual stress to a predetermined specification for residual stress representative of an acceptable manufactured coating, and determining whether the manufactured coating is acceptable for service or not based on whether the measured residual stress falls within or outside the specification.

8. In determining further usability of an engine-run multilayer thermal barrier coating in a gas turbine engine, the steps of:

determining residual stress proximate a relatively thin intermediate ceramic layer in the engine-run multilayer thermal barrier coating by directing a laser beam to pass through a relatively thick outer thermal insulating, different ceramic layer to illuminate said intermediate layer of said coating in a manner to cause species present in said intermediate layer to fluoresce to emit light that passes back through said outer thermal insulating layer, measuring the frequency shift of the light emitted by the fluorescing species after it passes through said outer thermal insulating layer, comparing the measured frequency shift of the intermediate layer to the frequency shift determined on a reference material under controlled stress states to assess relative residual stress in the measured coating without need to remove remaining thermal insulating layer from said engine-run coating, comparing the assessed residual stress to a predetermined specification for residual stress representative of a engine-run coating having remaining useful service life, and determining whether the engine-run coating is acceptable or not for return to further engine service based on whether the measured residual stress falls within or outside the specification.

9. In a non-destructive measurement method for determining acceptability of a multilayer thermal barrier coating having a relatively thin intermediate ceramic layer, a relatively thick outer thermal insulating, different ceramic layer overlying said intermediate layer and at least one of a bondcoat and superalloy substrate underlying said intermediate layer, the steps comprising directing a laser beam to pass through said outer thermal insulating layer to illuminate said intermediate layer of said coating in a manner to cause species incorporated in said intermediate layer from at least one of said bondcoat and said superalloy substrate to fluoresce to emit light that passes back through said outer thermal insulating layer, measuring the frequency shift of the light emitted by the fluorescing species after it passes through said outer thermal insulating layer, comparing the measured frequency shift of said intermediate layer to the frequency shift determined on a reference material under controlled stress states to assess relative residual stress in the measured coating without need to remove said thermal insulating layer from said coating, comparing the assessed residual stress to a predetermined specification for residual stress representative of an acceptable thermal barrier coating, and determining whether the thermal barrier coating is acceptable for use or not based on whether the measured residual stress falls within or outside the specification.

10. The method of any one of claims 7, 8, and 9 wherein the laser beam is directed at said intermediate layer having a thickness of about 0.1 to about 10 microns.

* * * * *

UNITED STATES PATENT AND TRADEMARK OFFICE
CERTIFICATE OF CORRECTION

PATENT NO : 6,072,568
DATED : June 6, 2000
INVENTOR(S): Neil E. PATON et al.

It is certified that error appears in the above-identified patent and that said Letters Patent is hereby corrected as shown below:

Column 7, Line 19: Change "underling" to ---underlying---.

Signed and Sealed this

Twenty-fourth Day of April, 2001

Attest:

NICHOLAS P. GODICI

Attesting Officer  Acting Director of the United States Patent and Trademark Office